(12) United States Patent
Dempster

(10) Patent No.: US 6,778,926 B2
(45) Date of Patent: Aug. 17, 2004

(54) CALIBRATION METHODS AND APPARATUS FOR PLETHYSMOGRAPHIC MEASUREMENT CHAMBERS

(75) Inventor: Philip T. Dempster, Concord, CA (US)

(73) Assignee: Life Measurement, Inc., Concord, CA (US)

(*) Notice: Subject to any disclaimer, the term of this patent is extended or adjusted under 35 U.S.C. 154(b) by 0 days.

(21) Appl. No.: 10/036,161

(22) Filed: Dec. 31, 2001

(65) Prior Publication Data

US 2003/0125891 A1 Jul. 3, 2003

(51) Int. Cl.[7] .............................................. G06F 19/00
(52) U.S. Cl. ....................................................... 702/97
(58) Field of Search ............................ 702/97; 600/529, 600/533, 534, 323, 536, 587; 73/149, 579, 433; 424/145, 85; 514/84; 128/716; 364/564

(56) References Cited

U.S. PATENT DOCUMENTS

| | | | |
|---|---|---|---|
| 4,184,371 A | | 1/1980 | Brachet |
| 4,369,652 A | | 1/1983 | Gundlach |
| 4,406,289 A | | 9/1983 | Wesseling et al. |
| 4,539,997 A | | 9/1985 | Wesseling et al. |
| 4,640,130 A | | 2/1987 | Sheng et al. |
| 4,676,253 A | | 6/1987 | Newman et al. |
| 4,841,982 A | * | 6/1989 | Nikiforov et al. ............ 600/529 |
| 4,888,718 A | | 12/1989 | Furuse |
| 4,972,842 A | * | 11/1990 | Korten et al. ................ 600/529 |
| 5,105,825 A | * | 4/1992 | Dempster .................... 600/587 |
| 5,379,777 A | | 1/1995 | Lomask |
| 5,450,750 A | | 9/1995 | Abler |
| 5,620,005 A | | 4/1997 | Ganshorn |
| 6,066,101 A | * | 5/2000 | Johnson et al. .............. 600/533 |
| 6,306,099 B1 | * | 10/2001 | Morris ........................ 600/529 |

OTHER PUBLICATIONS

Dewit et al., "Whole Body Air Displacement Plethysmography Compa5red with Hydrodensitometry for Body Composition Analysys," *Archives of Disease in Childhood* vol. 82 No. 2: pp. 159–164 (Feb. 2000).

(List continued on next page.)

Primary Examiner—John Barlow
Assistant Examiner—Tung Lau
(74) Attorney, Agent, or Firm—Fish & Neave; Mark D. Rowland; Douglas A. Oguss

(57) ABSTRACT

Methods and apparatus for calibrating volume measurement in a plethysmographic chamber are described. The present invention involves the use of a calibration volume chamber of known volume coupled to a plethysmographic measurement chamber in a plethysmographic measurement system for determining body composition, wherein a computer system calibrates the measurement system prior to conducting a volume measurement of a test subject, by measuring the chamber volume before and after opening an electronically controlled valve that connects the controlled calibration volume to the plethysmographic chamber, and comparing the measured chamber volumes based on the known reference volume.

62 Claims, 8 Drawing Sheets

OTHER PUBLICATIONS

Ellis et al., "Can Air–Displacement Plethysmography Replace Hydrodensitometry for Body Composition Analysis in Children and Adults," *Presented at Experimental Biology 2001 in Orlando*, Florida (abstract only).

Fields et al., "Body Composition Techniques and the Four–Compartment Model in Children," *Journal of Applied Physiology* vol. 89: pp. 613–620 (2000).

Gundiach et al., "The Plethysmometric Measurement of Total Body vol." *Human Biology* vol. 58 No. 5: pp. 783–799 (Oct. 1986).

Higgins et al., "Effect of Scalp and Facial Hair on Air Displacement Plethysmography Estimates of Percentage Body Fat," *Obes Res* May 2001; 9(5): 326–330.

http://academic.wsc.edu/hpls/glass_s/onlineped103/chapter4.htm, "What Fat is Linked to; Slides 4, 13–17, 20, 21, 23, 26, 28, 30" (Dec. 26, 2001).

http://www.geocities.com/HotSprings/5484/thesis/thesis2.htm, "Chapter II: Review of Literature on Body Composition" (Dec. 26, 2001).

http://hnrc.tufts.edu, "Laboratories and Programs: Body Composition Research Program" (Dec. 26, 2001).

http://www.nal.usda.gov/ttic/tektran/data/000009/27/0000092775.html, "Tektran Agriculture Research Service: Body Composition in Children and Adults by Air Displacement Plethysmography" (Dec. 26, 2001).

http://www.coe.uh.edu/~bsekula/pep6301/Ch.%2027%20Mkk.htm, "Body Composition Assessment" (Dec. 26, 2001).

http://www.odp.od.nih.gov/consensus/ta/015/015_intro.htm, "State of the Science Statements NIH Consensus Development Program: Bioelectrical Impedance Analysis in Body Composition Measurement—Dec. 12–14, 1994: 15. Bioelectrical Impedance Analysis in Body Composition Measurement" (Dec. 26, 2001).

http://brc.montana.edu/olympics/physiology/pb03.html, "Physiology & Psychology Performance Benchmarks: Body Composition and Body Mass" (Dec. 26, 2001).

LeCheminant et al., "Differences in Body Fat Percentage Measured Using Dual Energy X–Ray Absorptiometry and the BOD POD in 100 Women," *Presented at the American College of Sports Medicine 48th Annual Meeting, May 30–Jun. 2, 2001 in Baltimore, Maryland* (abstract only).

Lockner et al, "Comparison of Air–Displacement Plethysmography, Hydrodensitometry, and Dual X–ray Absorptionmetry for Assessing Body Composition of Children 10 to 18 Years of Age," *Annals of the New York Academy of Sciences* vol. 904—in Vivo Body Composition Studies: pp. 72–78 (May 2000).

Maddalozzo et al., "Concurrent Validity of the BOD POD and Dual Energy X–Ray Absorptiometry Techniques for Assessing the Body Fat Percentage in Young Women," *Presented at the American College of Sports Medicine 48th Annual Meeting, May 30–Jun. 2, 2001 in Baltimore, Maryland* (abstract only).

McCrory et al., "Evaluation of a New Air Displacement Plethysmograph for Measuring Human Body Composition," *Med Sci Sports Exerc*. Dec. 1995; 27(12): 1686–91.

McCrory et al., "Comparison of Methods for Measuring Body Composition Responses to Progressive Resistance Training in Hispanic Elders with Type 2 Diabetes," *Presented at Experimental Biology 2001 in Orlando, Florida* (abstract only).

Miyatake et al., "A New Air Displacement Plethysmograph for the Determination of Japanese Body Composition," *Diabetes Obes Metab* Nov. 1999; 1(6): 347–51.

Nicholson et al., "Estimation of Body Fatness by Air Displacement Plethysmography in African American and White Children," *Pediatric Research* vol. 50 No. 4: pp. 467–473 (2001).

Nunez et al., "Body Composition in Children and Adults by Air Displacement Plethysmography," Eur J Clin Nutr. May 1999; 53(5): 382–7.

Wagner et al., "Techniques of Body Composition Assessment: A Review of Laboratory and Field Methods," *Research Quarterly for Exercise and Sport*: pp. 135–149 (Jun. 1999).

Yee et al., "Calibration and Validation of an Air–Displacement Plethysmography Method for Estimating Percentage Body Fat in an Elderly Population: A Comparison among Compartmental Models 1–3," *American Journal of Clinical Nutrition* vol. 74: pp. 637–642 (2001).

Bailey et al., "Test–Retest Reliability of Body Fat Percentage Results Using Dual Energy X–Ray Absorptiometry and the BOD POD," *Presented at the American College of Sports Medicine 48th Annual Meeting, May 30–Jun. 2, 2001 in Baltimore, Maryland* (abstract only).

Biaggi et al., "Comparison of Air–Displacement Plethysmography with Hydrostatic Weighing and Bioelectrical Impedance Analysis for the Assessment of Body Composition in Healthy Adults 1–3," *American Journal of Clinical Nutrition* vol. 69: pp. 898–903 (1999).

Dempster et al., "A New Air Displacement Method for the Determination of Human Body Composition," *Med Sci Sports Exerc*. Dec. 1995; 27(12): 1692–7.

\* cited by examiner

CALIBRATION METHODS AND APPARATUS FOR PLETHYSMOGRAPHIC MEASUREMENT CHAMBERS

FIELD OF THE INVENTION

The present invention relates generally to apparatus and methods for providing repeatable measurements of volume within an enclosed chamber. More specifically, the present invention provides methods and apparatus for calibrating volume measurement in a plethysmographic measurement system.

BACKGROUND OF THE INVENTION

The assessment of body composition, including measurement of fat and fat-free mass, provides physicians with important information regarding physical status. Excess body fat has been associated with a variety of disease processes, such as cardiovascular disease, diabetes, hypertension, hyperlipidemia, kidney disease, and musculoskeletal disorders. Low levels of fat free mass have been found to be critically adverse to the health of certain at-risk populations, such as the elderly, infants, and those suffering from muscle wasting diseases.

Assessment of body composition has also been found to be useful in the context of evaluating and improving athletic performance. Generally, athletes require a high strength to weight ratio to achieve optimal athletic performance. Because body fat adds weight without a commensurate increase in strength, low body fat percentages have been emphasized within many athletic fields. However, too little body fat can result in deterioration of both health and athletic performance. Thus, accurate measurement of body composition has been found extremely useful in analysis of athletic performance.

A variety of methods are currently used in the assessment of body composition. One common method is a skinfold measurement, typically performed using calipers that compress the skin at certain points on the body. While non-invasive, this method suffers from poor accuracy on account of variations in fat patterning, misapplication of population specific prediction equations, improper site identification for compressing the skin, poor fold grasping, and the necessity for significant technician training to administer the test properly.

Another method employed is bioelectric impedance analysis ("BIA"). Bioelectric impedance measurements rely on the fact that the body contains intracellular and extracellular fluids that are capable of conducting electricity. By passing a high frequency electric current through the body, BIA determines body composition based on the bodies' measured impedance in passing current, and the known impedance values for human tissue. However, the accuracy of this method is greatly affected by the state of hydration of the subject, and variations in temperature of both the subject and the surrounding environment.

The most common method currently used when precision body mass measurements are required is hydrostatic weighing. This method is based upon the application of Archimedes principle, and requires weighing of the subject on land, repeated weighing of the subject under water, and an estimation of air present in the lungs of the subject using gas dilution techniques. However, hydrodensitometry is time consuming, typically unpleasant for the subjects, requires significant subject participation such as repeated, complete exhalation of air from the subject's lungs, requires considerable technician training and, due to the necessary facilities for implementation, is unsuitable for clinical practice. Further, its application to populations who would particularly benefit from body-mass measurement, such as the obese, elderly, infants, or cardiac patents, is precluded by the above concerns.

One technique offering particular promise in performing body mass measurement is the use of plethysmography. Plethysmographic methods determine body composition through application of Boyle's law to the differentiation in volume between the volume of an empty measurement chamber, and the volume of the chamber with the subject to be measured inside. Examples of this technique are disclosed in U.S. Pat. No. 4,369,652 issued to Gundlach, U.S. Pat. No. 5,450,750 issued to Abler, U.S. Pat. No. 4,184,371 issued to Brachet, and U.S. Pat. No. 5,105,825 issued to Dempster. This procedure, in contrast to hydrodensitometry, generally does not cause anxiety or discomfort in the subject, and due to the ease and non-invasiveness of the technique, can readily be applied to populations for whom hydrodensitometry is impractical.

However, such plethysmographic systems require very exact volume measurements to yield valid body composition results. In particular, calibration of the measurement chamber equipment used to generate the volume measurements for body composition analysis is necessary for achieving accuracy, on account of very small differences in measured volume yielding large differences in computed body composition. Although some efforts have been made in the field of calibration for plethysmographic systems, these methods are typically complicated, inexact, and/or inconvenient for the medical technicians who conduct plethysmographic body composition measurements by requiring manual activation and implementation of the calibration.

For example, Dempster, U.S. Pat. No. 5,108,825, discloses the use of a calibration volume structure that is manually placed in a plethysmographic reference chamber. However, this process is slow, cumbersome, and requires active participation by the medical technician to calibrate the system.

Ganshorn, U.S. Pat. No. 5,626,005, discloses a method of calibration for a plethysmographic chamber for measuring the volume of a subject's thorax-lung system. The method disclosed by Ganshorn involves the use of a harmonically oscillating piston pump that generates pressure fluctuations that simulates a test subject's breathing, and relies on these pressure fluctuations to calibrate a chamber pressure gauge based on the simulated breathing. However, this method is unnecessarily complex and not generally applicable to calibration of plethysmographic chambers used in the measurement of body composition.

Therefore, it would be desirable to provide a computer assisted calibration system for a whole body plethysmographic measurement chamber that provides accurate calibration of the measurement system.

It would further be desirable to provide a computer assisted calibration system for a whole body plethysmographic measurement chamber that does not require active, manual participation of medical technician to conduct the calibration.

SUMMARY OF THE INVENTION

It is an object of the present invention to provide a computer assisted calibration system for a whole body plethysmographic measurement chamber that provides accurate calibration of the measurement system.

It is another object of the present invention to provide a computer assisted calibration system for a whole body plethysmographic measurement chamber that does not require active, manual participation of medical technician to conduct the calibration.

These and other objects of the present invention are accomplished by proving computer assisted methods and apparatus for calibration of a plethysmographic measurement system using a calibration volume chamber.

The present invention generally consists of a calibration volume chamber of known, fixed volume coupled to a plethysmographic measurement chamber in a plethysmographic measurement system, wherein a computer system is used to calibrate the measurement system prior to conducting a volume measurement of a test subject, by measuring the chamber volume before and after opening (or alternatively, before and after closing) an electronically controlled valve that connects the controlled calibration volume to the plethysmographic chamber, and comparing the measured chamber volumes based on the known reference volume.

In one embodiment of the present invention, the actuation assembly for opening and closing the valve in response to a signal from the computer system is a cam and motor assembly coupled to a shaft that is mounted to the valve by means of a ball joint.

In a second embodiment of the present invention, the actuation assembly for opening and closing the valve in response to a signal from the computer system is a solenoid coupled to a shaft that is mounted to the valve by means of a ball joint.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
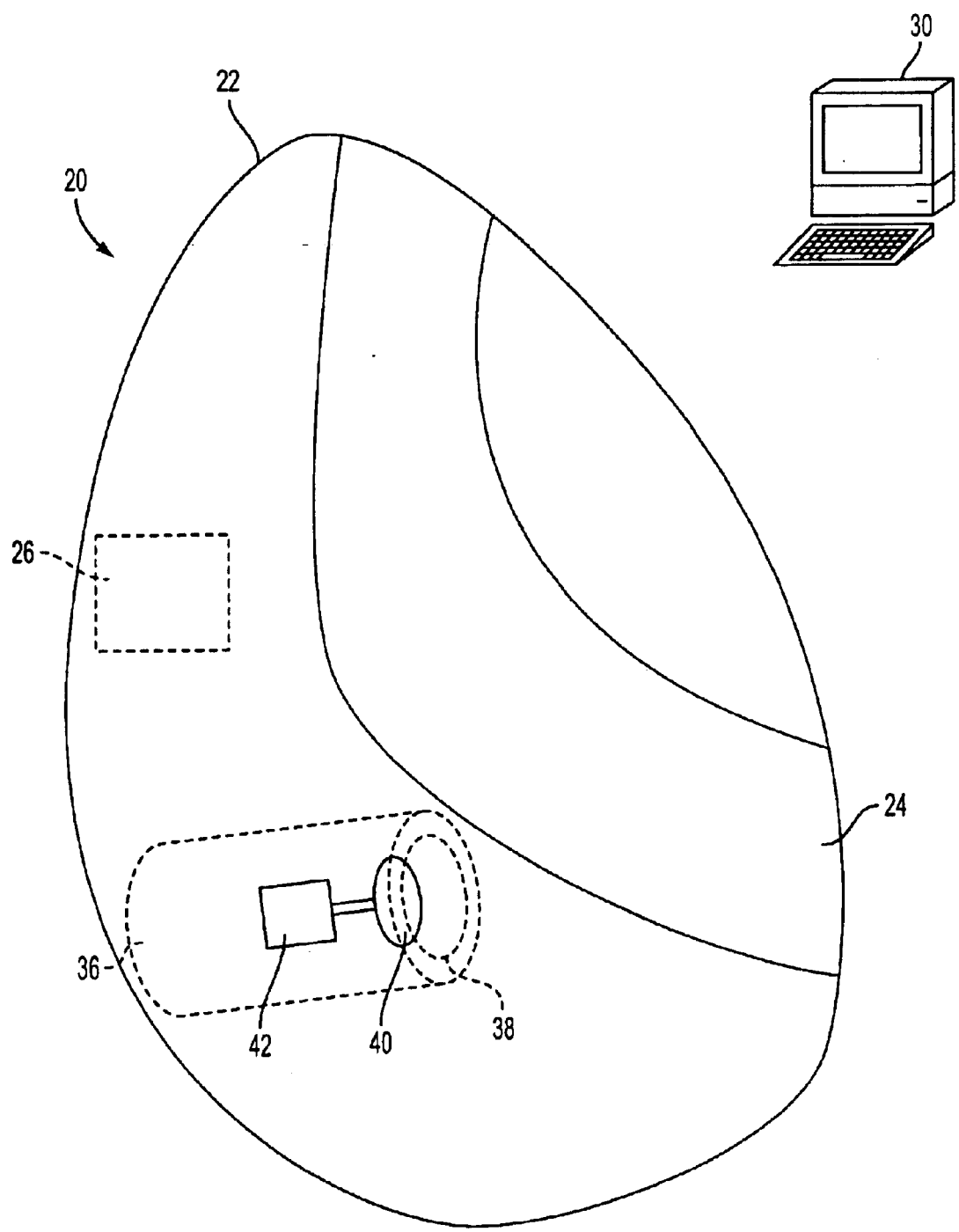
FIG. 1 is a representational view of an adult-sized plethysmographic chamber and control system in which embodiments of the present invention operate.

Referring now to FIG. 1, a representational view of an adult-sized plethysmographic chamber in which embodiments of the present inventions operate are described.

Plethysmographic measurement system 20 comprises measurement chamber 22, chamber door 24, plethysmographic measurement components 26, and computer 30. The operation of plethysmographic measurement components 26 is controlled by computer 30, which computer is operated by the medical technician performing the plethysmographic measurement. (As used herein, the term "medical technician" refers to any individual conducting the plethysmographic measurements of the test subject.)

Measurement components 26 can include such devices as an oscillating diaphragm or speaker, pressure transducers, their respective control systems, and other components necessary to conduct plethysmographic measurements. Further information regarding such plethysmographic measurement components, and the techniques used to derive volume and body composition measurements using them, are described in detail in Dempster, U.S. Pat. No. 5,105,825, assigned to Life Measurement Instruments, the specification of which is hereby incorporated by reference in its entirety. The algorithms used in conducting plethysmographic measurements are likewise well known to one of ordinary skill in the art, and therefore are not disclosed herein.

Housed within measurement chamber 22 is a calibration volume chamber 36, including an opening 38, a valve 40 for sealing and unsealing said opening, and valve actuation assembly 42 for opening and closing said valve in response to commands from computer 30.

When the medical technician initiates a measurement sequence, computer 30 is used to calibrate plethysmographic measurement system 20 prior to measuring the body composition of the test subject. The actual programming of computer 30 to conduct calibration of the plethysmographic measurement system is done in accordance with conventional programming techniques suitable for performing basic calculations and supplying control signals to the measurement components and actuation assembly of the present invention. These techniques are well known to one of ordinary skill in the art, and as such are not disclosed herein.

The calibration of the plethysmographic system can be, but need not be, performed without technician intervention. In a preferred embodiment, the calibration of the plethysmographic measurement system is conducted transparently to the medical technician, such that the calibration occurs automatically upon the technician initiating a plethysmographic measurement sequence.

Figure 2:
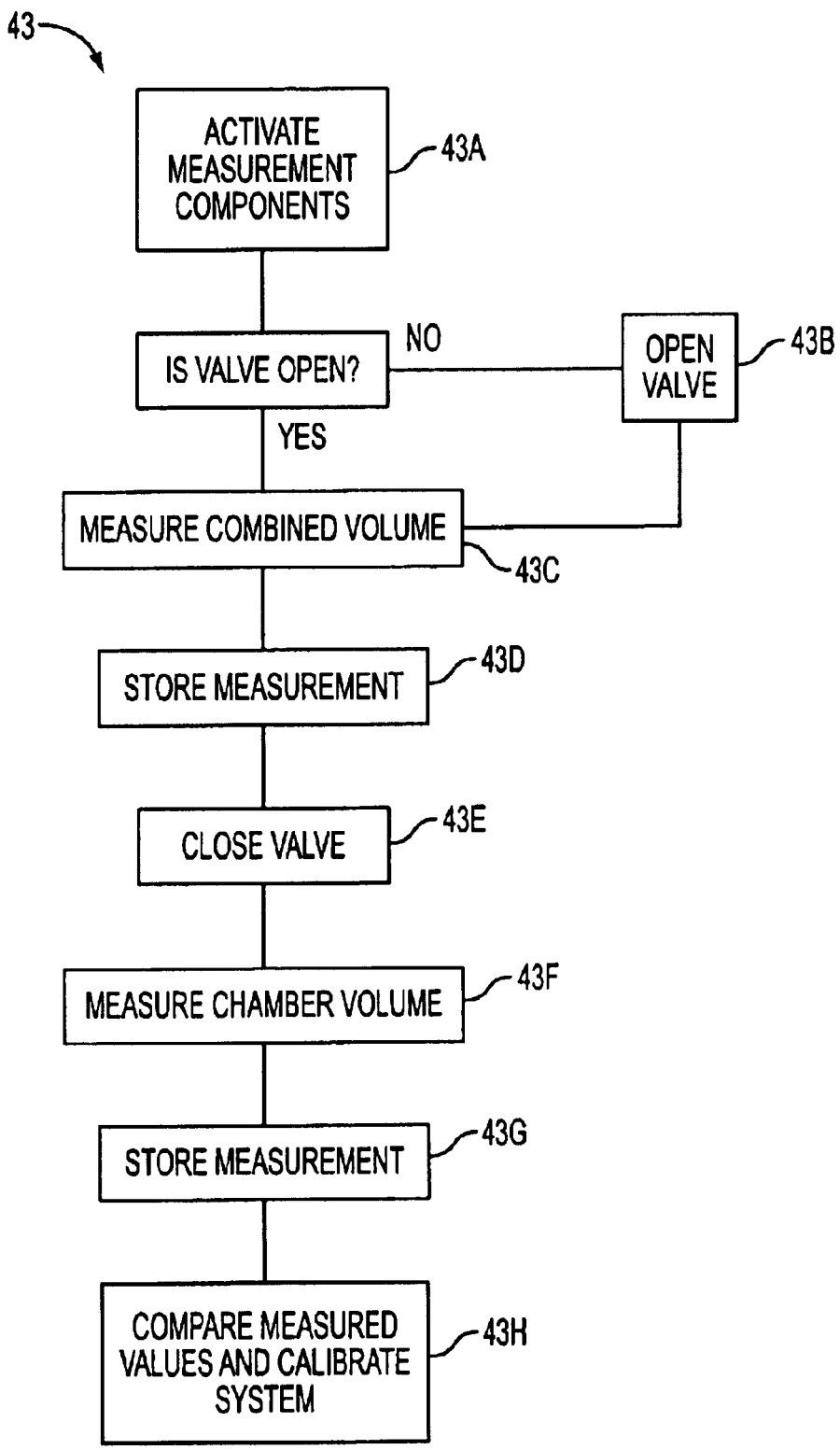
FIG. 2 is a flow chart describing the calibration sequence of one embodiment of the present invention.

As illustrated by flow chart 43 in FIG. 2, in a first embodiment of the present invention, computer 30 directs plethysmographic system 20 to first measure the volume of measurement chamber 22 when valve 40 is in the open position (i.e. with calibration reference volume 36 open to measurement chamber 22).

Specifically, in step 43A, computer 30 first activates the measurement components. In step 43B, computer 30 determines whether the valve is in the proper (open) state. If not, computer 30 sends a signal to actuation assembly 42 to open valve 40. In step 43C, computer 30 directs measurement components 26 to measure the combined volume of the measurement chamber and calibration volume chamber. In step 43D, computer 30 stores the values generated from the measurement in 43C. In step 43E, computer 30 sends an electrical signal to valve actuation assembly 42 to close valve 40, thereby reducing the net chamber volume. In step 43F, computer 30 directs measurement components 26 to measure the volume of measurement chamber 22. In step 43G, computer 30 stores the values generated by the measurement of step 43F. In step 43H, the measured volumes are then compared based on the known volume of calibration volume chamber 36. Based on the above comparison, computer 30 finalizes calibration of measurement system 20, and indicates to the technician that measurement of the test subject can begin.

The algorithms used to calibrate the plethysmographic measurement system based on the calibration processes of the present invention are known to those of skill in the art, and as such are not described herein.

Figure 3:
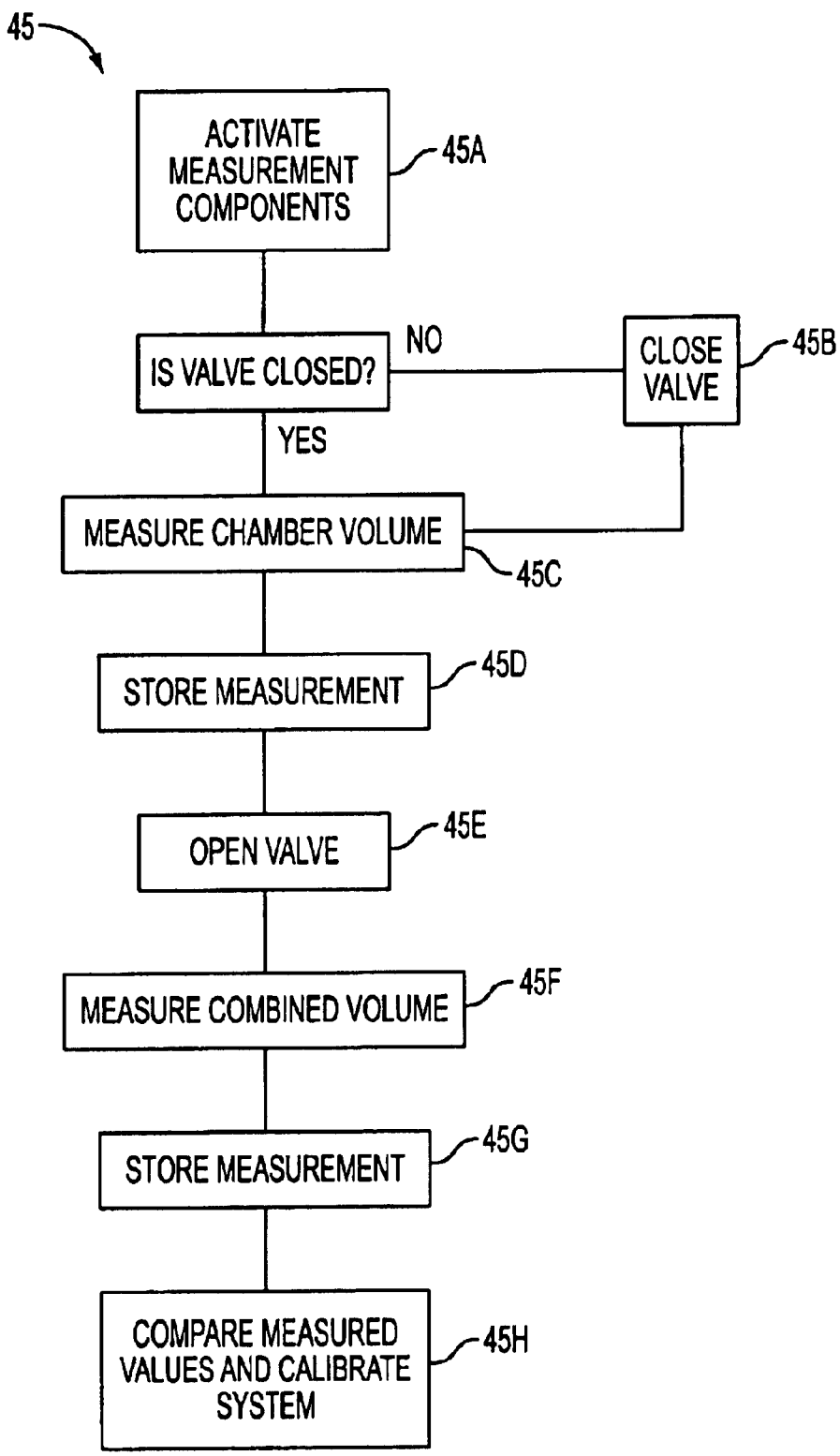
FIG. 3 is a flow chart describing the calibration sequence of a second embodiment of the present invention.

In an alternative embodiment of the present invention, illustrated in the flow chart of FIG. 3, computer 30 can direct plethysmographic system 20 to first measure the volume of measurement chamber 22 when valve 40 is in the closed position.

Specifically, in step 45A, computer 30 first activates the measurement components. In step 45B, computer 30 determines whether the valve is in the proper (closed) state. If not, computer 30 sends a signal to actuation assembly 42 to close valve 40. In step 45C, computer 30 directs measurement components 26 to measure the volume of measurement chamber 22. In step 45D, computer 30 stores the values generated from the measurement in 45C. In step 45E, computer 30 sends an electrical signal to valve actuation assembly 42 to open valve 40, thereby increasing the net chamber volume. In step 45F, computer 30 directs measurement components 26 to measure the combined volume of the measurement chamber and calibration volume chamber. In step 45G, computer 30 stores the values generated in step 45F. In step 45H, the measured volumes are then compared based on the known volume of calibration volume chamber 36. Based on the above comparison, computer 30 finalizes calibration of measurement system 20, and indicates to the technician that measurement of the test subject can begin. This calibration process results in calibration based on what is, in net effect, a negative volume measurement.

One of ordinary skill in the art would recognize that the are not limited to single measurements. Rather, multiple measurements of chamber volume with valve 40 open and closed can be used in accord with the present invention, with the system being calibrated based on the multiple data points generated by the measurements.

Further, one of ordinary skill in the art would recognize that the calibration methods disclosed herein could be conducted after plethysmographic measurement has been performed on the subject to be measured, because the methods of calibration disclosed herein are conducted by numerical calculations on measurement values. Thus, in such an embodiment, when the medical technician initiates the measurement sequence, measurements are first taken of the test subject in measurement chamber 22. The data generated in conducting this plethysmographic measurement of the test subject is stored on computer 30, after which the calibration methodology described above is conducted. Finally, the results of the calibration are applied to the measurements taken of the test subject to arrive at an accurate volume measurement for the subject.

Figure 4:
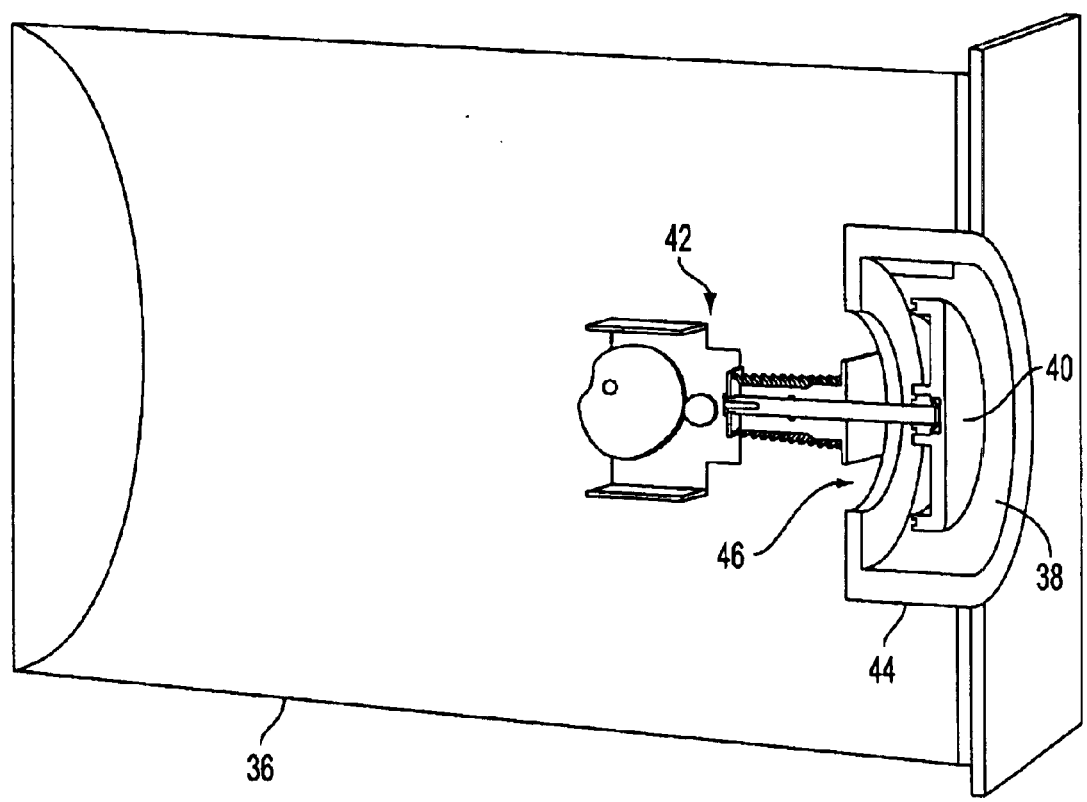
FIG. 4 is a cross-sectional view of one embodiment of the calibration volume chamber and valve actuation assembly of the present invention.

Referring now to FIG. 4, a cross-sectional view of a first embodiment of the calibration volume chamber and valve actuation assembly of the present invention is described. Calibration volume chamber 36 is a roughly cylindrical chamber with a known, stable internal volume. Although any shape can be used for reference volume chamber 36, it is preferred that the internal volume of reference volume chamber 36 be comparable to the volumes expected to be measured by the plethysmographic measurement system 20 in order to provide for more accurate calibration of the measurement system.

At one end of calibration chamber 36 is opening 38 that allows air to pass between calibration chamber 36 and plethysmographic chamber 22.

Mounted about the circumference of opening 38 is valve mount collar 42. Valve 40 is housed within valve mount collar 44. Valve 40 is coupled to valve actuation assembly 42, which opens and closes valve 40 in response to a signal from computer 30. At the end of valve mount collar 44 distal from said opening 38 is valve opening 46. When valve 40 is in the closed position, valve 40 creates a seal about valve opening 46 that completely seals off reference volume chamber 36 from plethysmographic chamber 22.

Figure 5A:
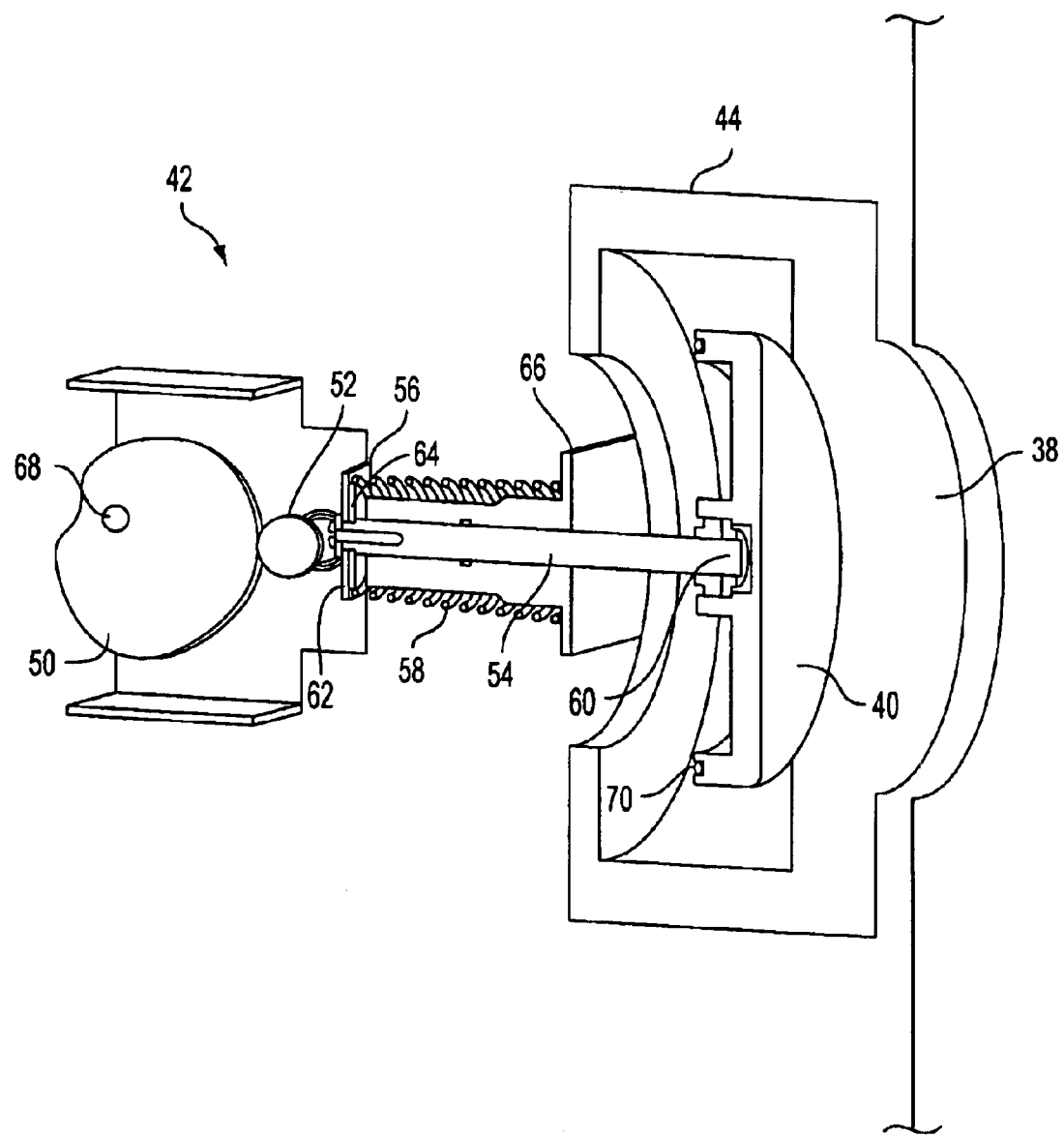
FIG. 5A is a detailed cross sectional view of one embodiment of the valve and valve actuation assembly of the present invention, with the valve in the open position.

Referring now to FIG. 5A, a detailed cross sectional view of the valve and valve actuation assembly of the present invention, in which valve 40 is in the open position, is described.

In this embodiment, valve actuation assembly 42 includes cam 50, cam follower 52, cam shaft 54, stamping 56 (which is further comprised of follower stamping 62 and spring stamping 64), cam spring 58, valve ball joint 60, and valve assembly mounting plate 66.

Valve 40 is coupled to a proximal end of cam shaft 52 by ball joint 60. Cam shaft 52 is further coupled to stamping 56 at the end of cam shaft 52 distal from valve 40.

Mounted around cam shaft 54 is cam spring 58, which is coupled at one end to spring stamping 64, and coupled at the opposite end to valve assembly mounting plate 66. Cam spring 58 generates an extension force against stamping 56.

Follower 52 is coupled to roller stamping 64. The force generated by cam spring 58 pushes against follower 52 by means of its coupling to spring stamping 62. This force ensures that follower 52 maintains solid contact with cam 50.

To open valve 40, cam motor 68 rotates cam 50 into an extended position, which exerts force on follower 52, thereby pushing on stamping 56 and compressing spring 58. This force applied to stamping 56 causes cam shaft 54 to move in the direction towards opening 38, thereby opening valve 40.

Figure 5B:
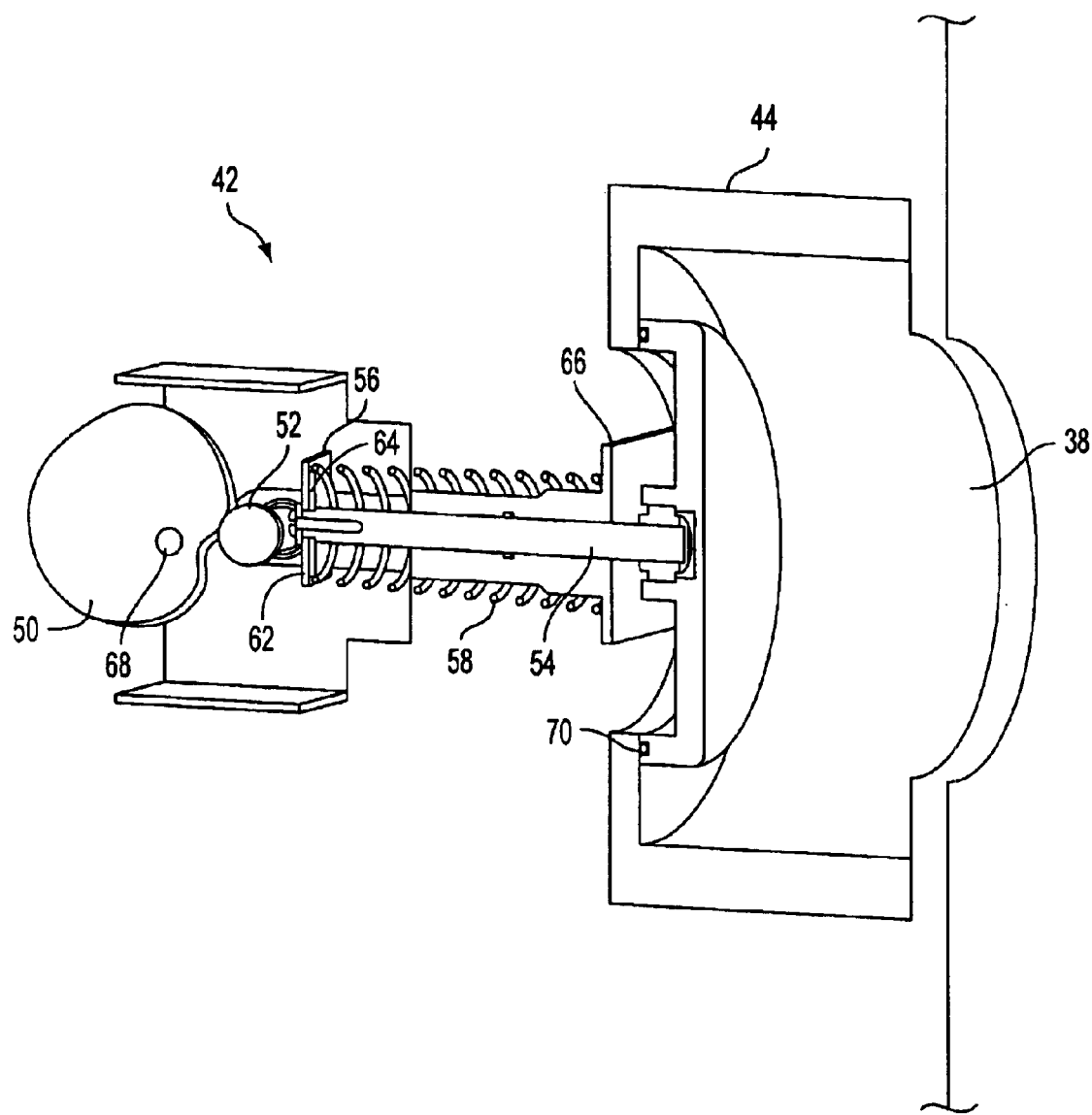
FIG. 5B is a detailed cross sectional view of one embodiment of the valve and valve actuation assembly of the present invention, with the valve in the closed position.

Referring now to FIG. 5B, a detailed cross sectional view of the valve and valve actuation assembly of the present invention, in which valve 40 is in the closed position, is described.

To close valve 40, cam motor rotates cam 50 into a retracted position, which allows cam spring 58 to push on stamping 56, and move cam shaft 54 until the edge of valve 40 makes contact with valve mount housing 44, thereby sealing off reference chamber 36 from plethysmography chamber 22.

In a preferred embodiment, a seal 70 is mounted about the circumference of valve 40, such that when valve 40 is in the closed position, seal 70 is compressed by valve 40 against valve mount housing 40, creating an air tight seal. Further, because ball joint 60 allows valve 40 to rotate with respect to cam shaft 54, valve 40 forms a repeatable, air tight seal against valve mount 40.

Figure 6:
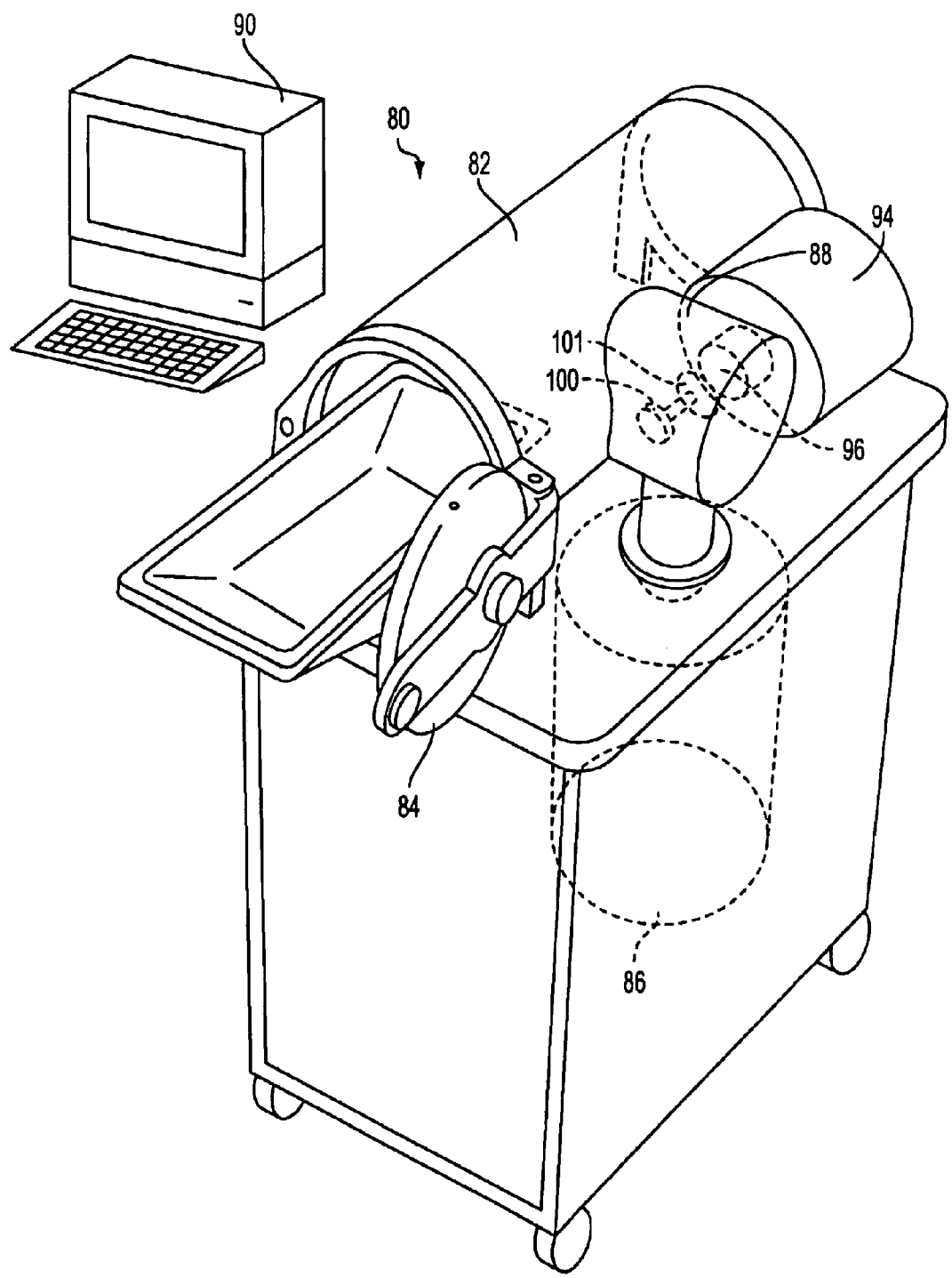
FIG. 6 is a representational view of the infant sized plethysmographic chamber in which the present inventions operate.

Referring now to FIG. 6, a representational view of an infant sized plethysmographic system in which embodiments of the present invention operate is described.

Plethysmographic system 80 comprises plethysmographic measurement chamber 82, chamber door assembly 84, plethysmographic measurement components 86, manifold 88 and computer 90. Calibration volume chamber 94 is coupled to measurement chamber 82 by manifold 88 (which also couples measurement components 86 to measurement chamber 82). Calibration chamber opening 96 allows air to pass from calibration volume chamber 94, through manifold 88, and into measurement chamber 82.

Valve actuation assembly 100 is coupled to valve 101, and seals and unseals opening 96 in response to commands from computer 90.

As disclosed in connection with the previous embodiment, when the medical technician initiates a body composition measurement sequence for a test subject, computer 90 calibrates plethysmographic measurement system 80 prior to measuring the body composition of the test subject, without the necessity of technician intervention to conduct the calibration.

Specifically, as described above in connection with the flow chart illustrated in FIG. 2, computer 90 directs plethysmographic system 80 to first measure the volume of measurement chamber 82 when valve 101 is in the open position. Computer 90 then sends an electrical signal to valve actuation assembly 100 to close valve 101, thereby reducing the net measurement chamber volume. The measured volumes are then compared to the expected volumes based on the known volume of calibration volume chamber 94. Based on this comparison, computer 90 finalizes calibration of measurement system 80, and indicates to the technician that measurement of the test subject can begin.

Similarly, the calibration system described above can calibrate measurement system 80 using the process illustrated in the flow chart of FIG. 3.

Figure 7:
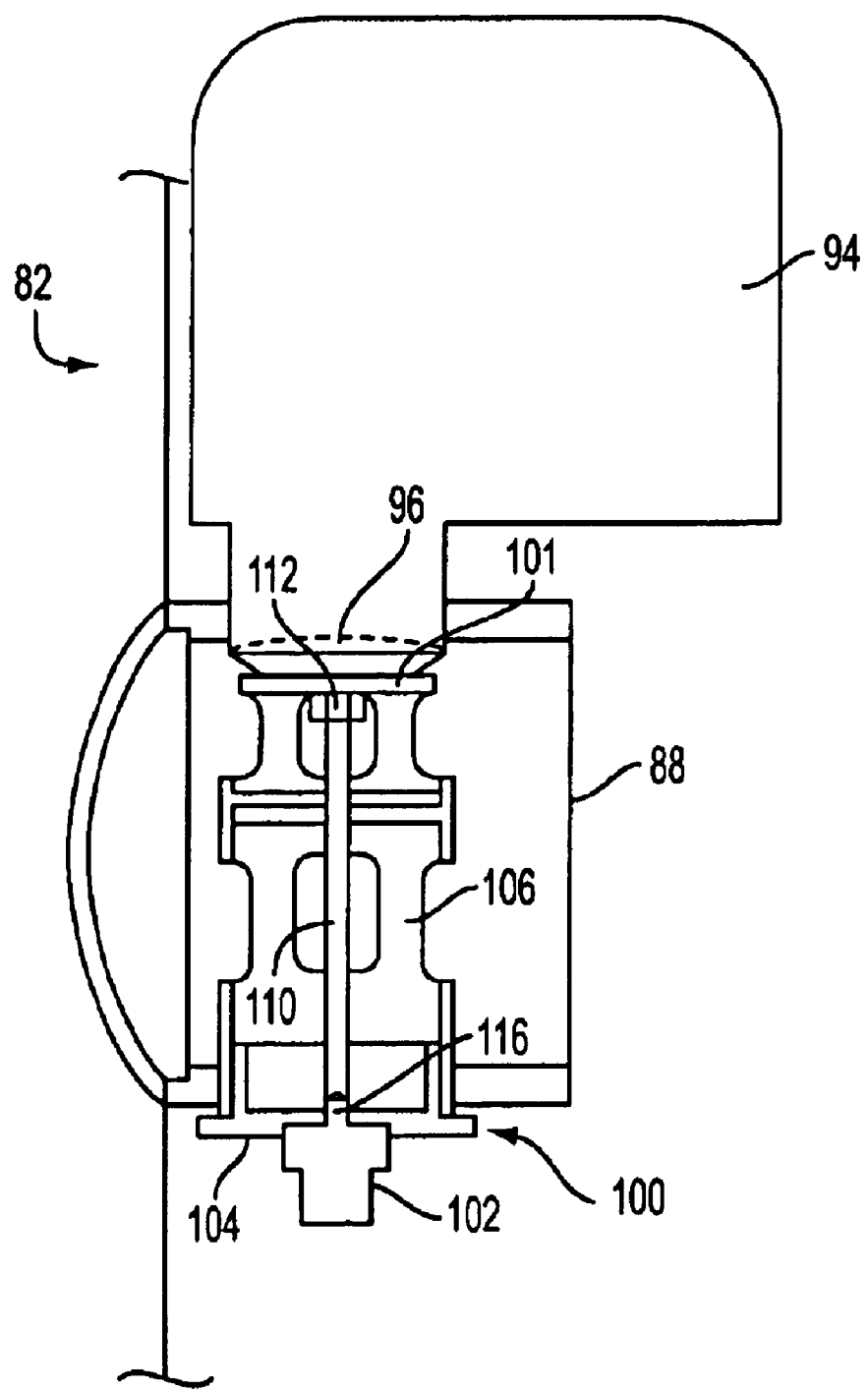
FIG. 7 is a cross sectional view of a second embodiment of the calibration volume and valve actuation assembly of the present invention.

Referring now to FIG. 7, a detailed cross-sectional view of the calibration volume and valve actuation assembly of the second embodiment of the present invention is described. As described above with respect to FIG. 4, measurement chamber 82 is coupled to calibration volume chamber 94 by manifold 88, and calibration volume chamber opening 96 allows air to pass from calibration volume chamber 94, through manifold 88, and into measurement chamber 82.

Valve actuation assembly 100 consists of solenoid 102, solenoid mount 104, inner manifold 106, shaft 110, and ball joint 112 coupled to valve 101. Valve actuation assembly 100 is housed within inner manifold 106, which is mounted across manifold 88 such that valve 101 can open and close calibration volume chamber opening 96.

Solenoid 102 is coupled to inner manifold 106 by solenoid mount 104. Solenoid 102 includes a plunger 116, which is coupled to shaft 110, such that the motion of shaft 110 tracks the motion of plunger 116. Shaft 110 is further coupled to valve 101 by means of ball joint 112 at the end of shaft 110 that is distal to solenoid 102. Valve 101 therefore opens and closes about calibration volume opening 96 in response to the motion of shaft 110.

Particularly, when plunger 116 is extended, it exerts a force on shaft 110, causing it to move in the direction of the force exerted by solenoid plunger 116. Shaft 110 thereby pushes on valve 101 against calibration chamber opening 96, sealing calibration volume chamber 94 from measurement chamber 82. Further, because ball joint 112 allows valve 101 to rotate with respect to shaft 110, valve 101 forms a repeatable, air tight seal against calibration volume chamber 94. Alternatively, any other type of pivotal joint, such as a universal joint, can be used in place of ball joint 112.

Similarly, when plunger 116 is retracted, it pulls shaft 110 away from the surface of calibration chamber opening 96, thereby opening valve 101 and allowing air to pass from calibration volume chamber 94 to measurement chamber 82.

One of ordinary skill in the art would recognize that the above disclosed embodiments for the valve actuator assemblies can be used interchangeably between infant and adult sized measurement chambers.

One of ordinary skill in the art would also recognize that alternative methods of controlling valves 40 and 101 can be used in accord with the present invention. For example, the use a pneumatic system that responds to a signal from a computer to open and close said valve is also contemplated by the present invention. Alternatively, a rotary motor coupled to ball screw, wherein the motor responds to a signal from a computer to open and close said valve, is also contemplated by the present invention.

Further, while preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method for calibrating a plethysmographic measurement system, the method comprising:

(a) measuring the combined volume of a plethysmographic measurement chamber and a known calibration volume coupled to said chamber by an opening to obtain a baseline volume measurement;

(b) sealing off said known volume from said chamber with an electronically controlled valve coupled to said opening;

(c) measuring the volume of said measurement chamber sealed off from said reference volume to obtain a comparison volume measurement;

(d) calibrating the plethysmographic measurement system based on the known calibration volume and a comparison of said baseline volume measurement and said comparison volume measurement.

2. The method of claim 1, wherein the calibration volume is calibration volume chamber with a known volume.

3. The method of claim 1 wherein sealing off the reference volume further comprises:

sending an electrical signal to an actuation assembly coupled to said electronically controlled valve, wherein said actuation assembly moves a shaft coupled between said assembly and said valve to close said valve against said opening.

4. The method of claim 1, wherein steps (a)–(d) occur without intervention of a medical technician conducting a plethysmographic measurement using said measurement system.

5. The method of claim 1, further comprising:

conducting a plethysmographic measurement of a test subject prior to measuring the combined volume of the plethysmographic measurement chamber and the known calibration volume coupled to said chamber to obtain a baseline volume measurement, and wherein calibrating the plethysmographic measurement system base on the known calibration volume and a comparison of said baseline volume measurement and said comparison volume measurement further comprises:

adjusting a result of the plethysmographic measurement of the test subject based on said calibration of the measurement system.

6. The method of claim 1, further comprising:

conducting a plethysmographic measurement of a test subject after calibration of the system.

7. The method of claim 2, wherein the actuation assembly further comprises:
a pneumatic system coupled to said shaft, wherein activation of the pneumatic system opens and closes said valve.

8. The method of claim 3, wherein the actuation assembly further comprises:
a cam;
a follower coupled between said cam and said shaft wherein rotation of the cam moves said shaft, and wherein movement of said shaft either opens or closes said valve.

9. The method of claim 3, wherein the actuation assembly further comprises:
a solenoid including a plunger, wherein said plunger is coupled to said shaft, and wherein movement of said plunger either opens or closes said valve.

10. The method of claim 3, wherein said shaft is coupled to said valve by a pivotal joint.

11. The method of claim 4, wherein steps (a)–(d) are conducted transparently to said medical technician.

12. A method for calibrating a plethysmographic measurement system, the method comprising:
(a) measuring the volume of a plethysmographic measurement chamber to obtain a baseline volume measurement, wherein an opening coupling said measurement chamber to a known calibrated volume has been sealed with an electronically controlled valve;
(b) unsealing the opening coupling said known volume to said measurement chamber with said electronically controlled valve;
(c) measuring the combined volume of the measurement chamber and the known calibration volume coupled to said chamber by said opening to obtain a comparison volume measurement;
(d) calibrating the plethysmographic measurement system based on the known calibration volume and a comparison of said baseline volume measure ent and said comparison volume measurement.

13. The method of claim 12, further comprising:
conducting a plethysmographic measurement of a test subject prior to measuring the combined volume of the plethysmographic measurement chamber and the known calibration volume coupled to said chamber to obtain a baseline volume measurement, wherein calibrating the plethysmographic measurement system based on the known calibration volume and a comparison of said baseline volume measurement and said comparison volume measurement further comprises:
adjusting a result of the plethysmographic measurement of the test subject based on said calibration of the measurement system.

14. The method of claim 12, further comprising:
conducting a plethysmographic measurement of a test subject after calibration of the system.

15. The method of claim 12, wherein the calibration volume is calibration volume chamber with a known volume.

16. The method of claim 12, wherein unsealing the opening coupling said known volume to said measurement chamber further comprises:
sending an electrical signal to an actuation assembly coupled to said electronically controlled valve, wherein said actuation assembly move a shaft coupled between said assembly and said valve to open said valve.

17. The method of claim 12, wherein steps (a)–(d) occur without intervention of a medical technician conducting a plethysmographic measurement using said measurement system.

18. The method of claim 14, wherein said shaft is coupled to said valve by a pivotal joint.

19. The method of claim 16, wherein the actuation assembly further comprises:
a cam;
a follower coupled between said cam and said shaft wherein rotation of the cam moves said shaft, and wherein movement of said shaft either opens or closes said valve.

20. The method of claim 16, wherein the actuation assembly further comprises:
a solenoid including a plunger, wherein said plunger is coupled to said shaft, and wherein movement of said plunger either opens or closes said valve.

21. The method of claim 16, wherein the actuation assembly further comprises:
a pneumatic system coupled to said shaft, wherein activation of the pneumatic system opens and closes said valve.

22. The method of claim 17, wherein steps (a)–(d) are conducted ransparently to said medical technician.

23. The calibration system of claim 18, wherein motion of the shaft away from said cam causes said valve to open.

24. A calibration system for calibrating a plethysmographic measurement system, the calibration system comprising:
a computer;
a calibration volume chamber of known volume, including an opening coupling said calibration volume chamber to a plethysmographic measurement chamber;
an electronically controlled valve responsive to said signals from said computer, for sealing and unsealing said opening;
wherein said computer initializes a calibration sequence prior to conducting a lethysmographic measurement of a test subject.

25. The calibration system of claim 24, wherein the volume chamber has a fixed volume.

26. The calibration system of claim 24, wherein the electronically controlled valve further comprises:
a valve actuation assembly; and
a valve coupled to said actuation assembly.

27. The calibration system of claim 24, wherein said valve is coupled to said valve actuation assembly by a shaft.

28. The calibration system of claim 24, wherein the valve further includes a seal about the circumference of said valve.

29. The calibration system of claim 24, wherein said calibration sequence is conducted without interaction by a medical technician.

30. The calibration system of claim 25, wherein the calibration volume chamber is housed within said plethysmographic measurement chamber.

31. The calibration system of claim 25, wherein the calibration volume chamber is mounted on the outside of said plethysmographic measurement chamber.

32. The calibration system of claim 25, further comprising:
a manifold, coupled between said calibration volume chamber and said plethysmographic measurement chamber.

33. The calibration system of claim 26, wherein the valve actuation assembly further comprises:
a cam;
a follower coupled to said cam; wherein rotation of said cam causes said valve to open or close.

34. The calibration system of claim 26, wherein the valve actuation assembly further comprises:
a solenoid, including a plunger, wherein said plunger is coupled to said valve and wherein motion of said plunger causes said valve to open or close.

35. The calibration system of claim 26, wherein the pneumatic device is coupled to a shaft, and wherein the action of said pneumatic device generates motion in said shaft, causing said valve to open or close.

36. The calibration system of claim 26, wherein the actuation assembly comprises:
a rotary motor;
a ball screw coupled to said rotary motor;
wherein the operation of the motor causes said valve to open or close.

37. The calibration system of claim 27, wherein said valve is coupled to said shaft by a pivotal joint.

38. The system of claim 33, further comprising:
a shaft, coupled between said follower and said valve, and wherein rotation of said cam causes said shaft to move, opening and closing said valve.

39. The calibration system of claim 33, wherein the cam is rotated by a motor.

40. The calibration system of claim 34, wherein plunger extends or retracts in response to signals from said computer.

41. The calibration system of claim 34, further comprising:
a shaft, coupled between said solenoid plunger and said valve, and wherein said shaft moves in response to the extension or retraction of said plunger.

42. The system of claim 38, further comprising:
an extension spring, mounted about said shaft, that applies a force to said follower to ensure contact between said follower and said shaft.

43. The calibration system of claim 38, wherein motion of the shaft towards said cam causes said valve to open.

44. The calibration system of claim 39, wherein the motor is responsive to signals from said computer.

45. The calibration system of claim 41, wherein motion of said shaft causes said valve to open or close.

46. The calibration system of claim 45, wherein extension of said plunger causes said valve to open.

47. The calibration system of claim 46, wherein extension of said plunger causes said shaft to close.

48. The calibration system of claim 47, wherein the valve actuation assembly further comprises:
a pneumatic device wherein the action of said pneumatic device causes said valve to open or close.

49. The calibration system of claim 36, further comprising:
a shaft, coupled between said ball screw and said valve, wherein operation of the motor generates motion in said shaft, causing said valve to pen or close.

50. A plethysmographic measurement system for conducting body composition measurements, comprising:
a plethysmographic measurement chamber;
measurement components, for measuring the volume of said test subject;
a calibration volume chamber, coupled to said measurement chamber by an opening;
an electronically controlled valve for sealing and unsealing said opening;
a computer for operating said measurement system;
wherein said computer initiates and runs a calibration sequence using said calibration volume and said valve, without intervention by a medical technician.

51. The measurement system of claim 50, wherein the calibration volume chamber is housed within the plethysmographic measurement chamber.

52. The measurement system of claim 50, wherein the calibration volume chamber is mounted to the outside of said plethysmographc measurement chamber.

53. The measurement system of claim 50, further comprising:
a valve actuation assembly for opening and closing said valve in response to signal from said computer.

54. The measurement system of claim 53, wherein the valve actuation assembly further comprises:
a cam;
a follower coupled between said cam; and said valve, wherein rotation of said cam causes said valve to open or close.

55. The measurement system of claim 53, wherein the valve actuation assembly further comprises:
a solenoid, including a plunger, wherein said plunger is coupled to said valve, and wherein motion of said plunger causes said valve to open or close.

56. The calibration system of claim 53, wherein the valve actuation assembly further comprises:
a pneumatic device wherein the action of said pneumatic device causes said valve to open or close.

57. The calibration system of claim 53, wherein the actuation assembly comprises:
a rotary motor;
a ball screw coupled to said rotary motor;
wherein the operation of the motor causes said valve to open or close.

58. The measurement system of claim 54, further comprising:
a shaft coupled between said follower and said valve, wherein said shaft moves in response to rotation of said cam, and wherein movement of said shaft causes said valve to open or close.

59. The calibration system of claim 55, wherein plunger extend or retracts in response to signals from said computer.

60. The calibration system of claim 55, further comprising:
a shaft, coupled between said solenoid plunger and said valve, and wherein said shaft moves in response to the extension or retraction of said plunger.

61. The calibration system of claim 60, wherein motion of said shaft causes said valve to open or close.

62. The calibration system of claim 57, further comprising:
a shaft, coupled between said ball screw and said valve, wherein operation of the motor generates motion in said shaft, causing said valve to open or close.

* * * * *